(12) United States Patent
Beigel et al.

(10) Patent No.: US 7,403,280 B2
(45) Date of Patent: Jul. 22, 2008

(54) FIBER COUPLING INTO BENT CAPILLARY

(75) Inventors: Betram Beigel, Karlsruhe (DE); Beno Mueller, Ettlingen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 394 days.

(21) Appl. No.: 11/266,679

(22) Filed: Nov. 3, 2005

(65) Prior Publication Data

US 2007/0097361 A1    May 3, 2007

(51) Int. Cl.
   *G01N 1/10* (2006.01)
(52) U.S. Cl. .................. 356/246; 356/246; 356/440; 356/432; 385/70; 385/115
(58) Field of Classification Search .......... 356/246, 356/410, 440–442, 432, 436, 445; 385/70–73, 385/115–130
See application file for complete search history.

(56) References Cited

U.S. PATENT DOCUMENTS

| 4,477,186 | A | * | 10/1984 | Carlson | 356/246 |
| 5,141,548 | A | * | 8/1992 | Chervet | 65/108 |
| 6,281,975 | B1 | | 8/2001 | Munk | 356/440 |
| 6,416,234 | B1 | * | 7/2002 | Wach et al. | 385/70 |
| 6,526,188 | B2 | * | 2/2003 | Dourdeville et al. | 356/436 |

FOREIGN PATENT DOCUMENTS

EP    0089157    9/1983

* cited by examiner

*Primary Examiner*—L. G. Lauchman
*Assistant Examiner*—Iyabo S Alli
(74) *Attorney, Agent, or Firm*—Marc Bobys

(57) ABSTRACT

A fluidic device is provided which is adapted to subject a fluid to light. It generally comprises a capillary that is adapted for conducting the fluid and which furthermore and comprises at least one bending and at least one waveguide having an end face that is adapted for at least emitting or receiving light. The end face is coupled with the bending for emitting light into the fluid or receiving light from the capillary.

27 Claims, 5 Drawing Sheets

FIBER COUPLING INTO BENT CAPILLARY

FIELD OF THE INVENTION

The present invention relates to fluidic devices for subjecting a fluid to light.

DISCUSSION OF THE BACKGROUND ART

Photochemical reactions including photo polymerization or photochemical cleavage of molecules in smaller units, as well as optical detection of fluids or components comprised in fluidic substances are well described in the literature and known to those skilled in the art. They are carried out in detecting devices or in reactors having technical size or lab size. Devices for microfluidic applications are known and described. These devices ought to meet the requirements which result from sophisticated techniques:

Optical detection of fluidic samples succeeding to chemical separation or preparation is a most preferred technique since it is applicable without interfering in the chemical system being in the focus. In order to perform such optical detection generally a measuring chamber for the reception of the fluid, a light emitting device and a light receiving device are needed. Performing online detection means designing a measuring chamber as a flow through cell. One may perform transmission or absorption measurements which are corresponding as indicated by optical laws such as Beer's law, which is known to those skilled in the art. Whichever technique is chosen, it presumes guiding light through the sample, accordingly a light path between a light emitting and a light receiving means is required. Simplified, light emitting and light receiving means comprise a light source, detector and the corresponding waveguides. Applying Beer's law furthermore means knowing precisely the geometrical dimensions of the measuring device as far as they are needed to determine optical coefficients such as e.g. extinction. The extinction coefficient refers to the relation of light throughput through a volume of fluid having certain physical and chemical properties. The length of the light path, correlated with said volume of fluid and being correlated with the concentration of the components in the fluid, is accordingly a key parameter in optical detection, being comprised in said extinction coefficient.

The length of the light path is a key parameter in photochemistry, too, since the light throughput frequently determines the yield of a reaction or the conversion: The above cleavage reaction may be performed with an optimal conversion rate if the relation light path-to-reactor volume is optimized, which comprises length of a flow through cell which serves as photo reactor.

A number of microfluidic devices has already been described in the art, the below devices referring on the function of an optical fluidic device as detection device:

A device for microfluidic optical detections is described in U.S. Pat. No. 6,281,975, to Munk. He describes a capillary flow cell with protruding bulb ends providing a high light throughput entrance window for the cell, aiming for an improved sample illumination.

EP 0,089,157 to Le Febre discloses an optical detector cell for determining the presence of a solute in a sample fluid, for the particular application in miniature chromatographic and micro spectroscopic applications. An optical flow path which is parallel to the fluid flow path is provided, allowing maximizing of the sample corresponding to a fixed sample volume, whereby the ability results to measure low threshold concentrations in solutes.

U.S. Pat. No. 4,477,186 to Carlson refers to a photometric cuvette for optical analysis of through flowing media, designed for the measurement of minimum sample amounts.

SUMMARY OF THE INVENTION

It is an object of the invention to provide an improved fluidic device. The object is solved by the independent claims. Preferred embodiments are shown by the dependent claims.

According to embodiments of the present invention, a fluidic device is provided which is designed to perform optical analytics as well as to carry out photochemical applications with fluids. A bent capillary conducts the fluid and a waveguide with a suitable end face is coupled to said capillary at the bending, accordingly permitting to emit light into the capillary and into the fluid, respectively, or to receive light from the capillary. The bent capillary which provides a light path due to the coupling with waveguides. It advantageously permits the integration of a custom tailored fluidic device serving as measuring tool, detection device or photochemical reaction device as part of a master device, its functionality depending on the number of couplings with waveguides and on the performance of the correspondence between the waveguides or, respectively, between a pair of waveguides.

Another embodiment of the present invention refers to a fluidic device comprising a bent capillary and being coupled to a waveguide and the bending, accordingly this embodiment suits for measuring and detection applications as well as for performing photochemistry, but it is furthermore designed as a flow through cell, accordingly having an inlet and an the outlet. A conduit that is adapted for supplying the capillary with fluid or for removing the fluid is connected to the corresponding in- or outlet port makes it possible to integrate the device in a corresponding master device and, hence, permits to work online, without disturbing running processes.

Furthermore, a method is disclosed for manufacturing the fluidic device of the embodiments of the present invention. The method refers to the coupling of the waveguide end face with said bending, wherein the coupling is to be done in a way that emitting light into the fluid and receiving light from the capillary is realized disturbance free and wherein at the same leaking of the capillary is excluded.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION OF THE PREFERRED EMBODIMENT

Photochemical reactions and optical detection of fluids or components comprised in fluidic substances are applications that are apparently completely different from each other with respect to their execution and the focused result. Nevertheless, there are similarities in photochemical reactions and in certain detection processes, which permit the designing of fluidic devices suitable to be used for carrying out both of said applications:

Generally, the embodiments of the present invention refer to fluidic devices comprising a capillary and at least one waveguide which is docked to the capillary or which is inserted into the capillary, whereby a definite portion of the capillary serves as optical light path. This optical light path may is used in both of said applications: whether as detection path or as reaction path. So, the device of the embodiments of the present invention may be applicable as well for photochemical reactions as for optical detection of fluids or components comprised in fluidic substances.

Figure 1A:
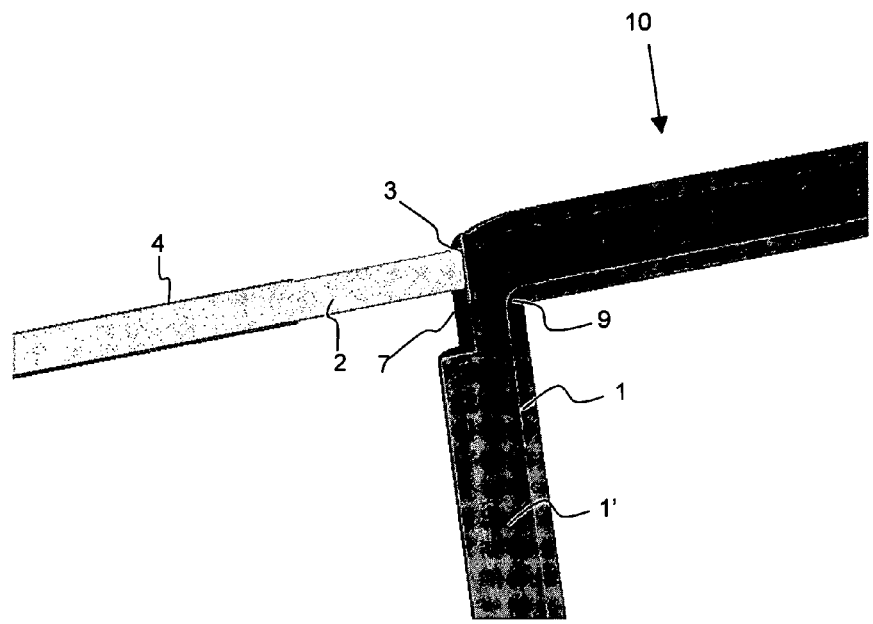
FIG. 1a shows a cross sectional side view of the fluidic device with a waveguide being docked to the capillary via a large docking spot.

FIG. 1a shows a first option of a fluidic device 10 which is adapted to conduct a fluid and to subject it to light. Said fluidic device 10 comprises the capillary 1 enclosing a fluid flow path 1' for fluid conduction. The capillary 1 is made of a material being one of an amorphous fluoropolymer or quartz, providing total reflectance of the light inside said capillary 1. Total reflectance of light inside the capillary should be a general feature of the embodiments of the present invention.

Said capillary 1 of FIG. 1a has one bending 9 which has a docking flat spot 7 at its outer curve and which docking flat spot 7 is designed to provide a coupling of the end face 3 of said waveguide 2 with the outer surface of the capillary 1. The waveguide 2 is adapted for emitting or receiving light. Whether the function of the waveguide is emitting or receiving light depends on the further components of the device 10, which are not shown herein: Either the waveguide is connected to a light source, thereby being a light emitting device, or the waveguide is connected to a light detecting device, thereby it serves as a light receiving device. The light emitting source or the detector may be connected directly to the capillary or in a certain distance and the connection may include an interconnecting element.

The waveguide 2 being depicted in FIG. 1a, is a quartz fiber. Advantageously it is coated partially with a coating 4 which prevents loss of light and which shelters the waveguide 2 of being damaged, too. The coating 4 could be polyimide material, a coating dye or any other suitable coating material which provides total reflectance of the light inside the waveguide 2.

Generally, the waveguides of the herein depicted embodiments could be quartz fibers and they could be coated as described before.

Figure 1B:
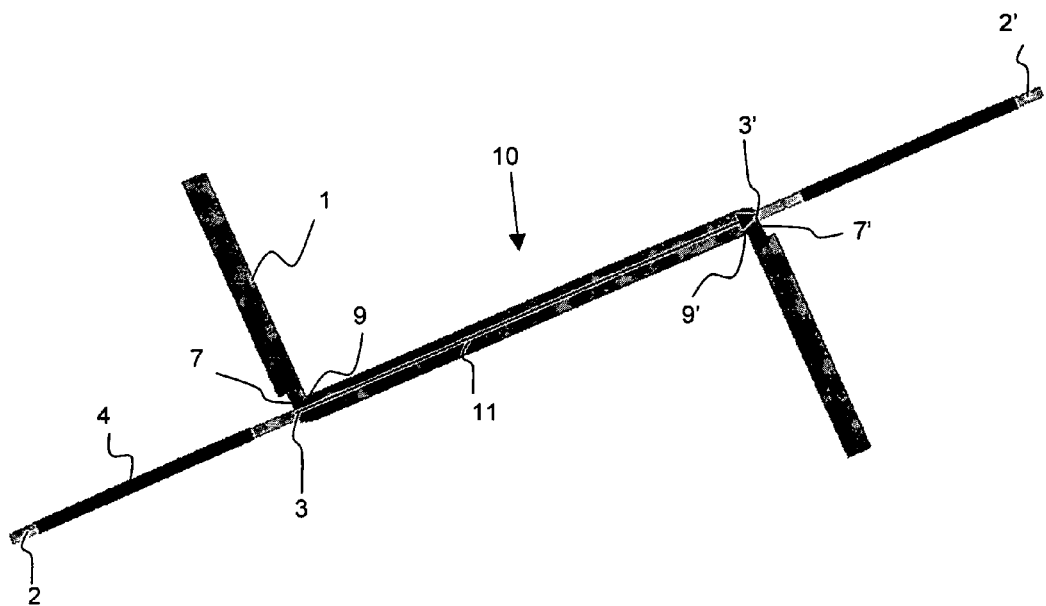
FIG. 1b shows a side view of the fluidic device with a couple of waveguides being docked via two docking spots to a capillary having two bendings.

FIG. 1b displays an embodiment of the capillary 1 which has two bendings 9,9'. Herein, the bending angle is approximately 90°, but it could also be larger or smaller. The capillary 1 is furthermore equipped with a couple of two waveguides 2,2' which are docked with their end faces 3,3' at the docking spots 7,7' to the capillary 1 and, hence, are adapted to communicate optically with each other inside the fluid flow path 1'. Accordingly a light path 11 of a distance d is provided between the end faces 3,3' of the facing waveguides 2,2' being docked to the capillary outside. Herein, the distance d is congruent to the space between the bendings 9,9'.

Optical communication of a couple of facing waveguides is not needed necessarily in all cases: If the device is designed to perform photochemical reactions only, one may use the waveguides as light emitting devices, coupling them to one or more light sources then. This setting of the waveguides as light emitting devices may be generally used if the embodiments of the present invention are applied in photochemical and not in detection applications. One may wish to select light sources emitting light of certain wavelengths, which correspond optimally with the requirements of the photoreaction to be performed. Those skilled in the art will know which wavelengths and, hence, which amount of photo energy is needed, to perform cleavage of particular organic molecules, e.g.

Figure 1C:
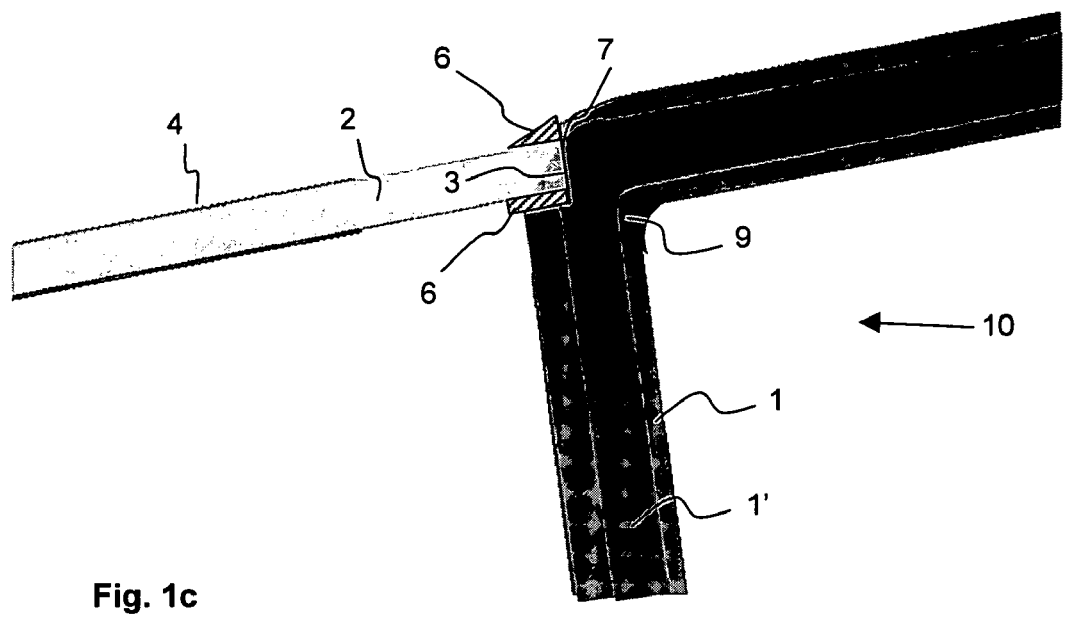
FIG. 1c shows a cross sectional side view of the fluidic device with a waveguide being docked to the capillary via a small docking spot, the docking comprising an extra sealing.

The embodiment of FIG. 1a is picked up and extended, quasi "doubled" in FIG. 1c:

FIG. 1c shows a cross sectional side view of the fluidic device 10 with a small docking flat spot 7, the cross-sectional area of the docking flat spot 7 corresponding to the cross-sectional area of the waveguide. By docking the waveguide 2 to the docking flat spot 7, the cross-sectional areas were brought in congruence with each other, providing an optimal light coupling into the capillary or receiving of light from the capillary.

The docking of the herein disclosed embodiments is generally provided at the docking flat spot. It may comprise adding of a docking material or extra "sealing", respectively:

FIG. 1c shows clearly that an extra sealing 6 is provided around the end face 3 of the waveguide 2, which is applied directly at the coupling, preventing an unwanted exit of light and stabilizing the coupling of the components waveguide 2 and capillary 1. The sealing material could be advantageously an extra volume of molten quartz material, or a polymeric material, in particular a polyetherketone such as polyetheretherketone, or a suitable gluing material. Of course, other suitable sealing materials might be applied, too.

Figure 2A:
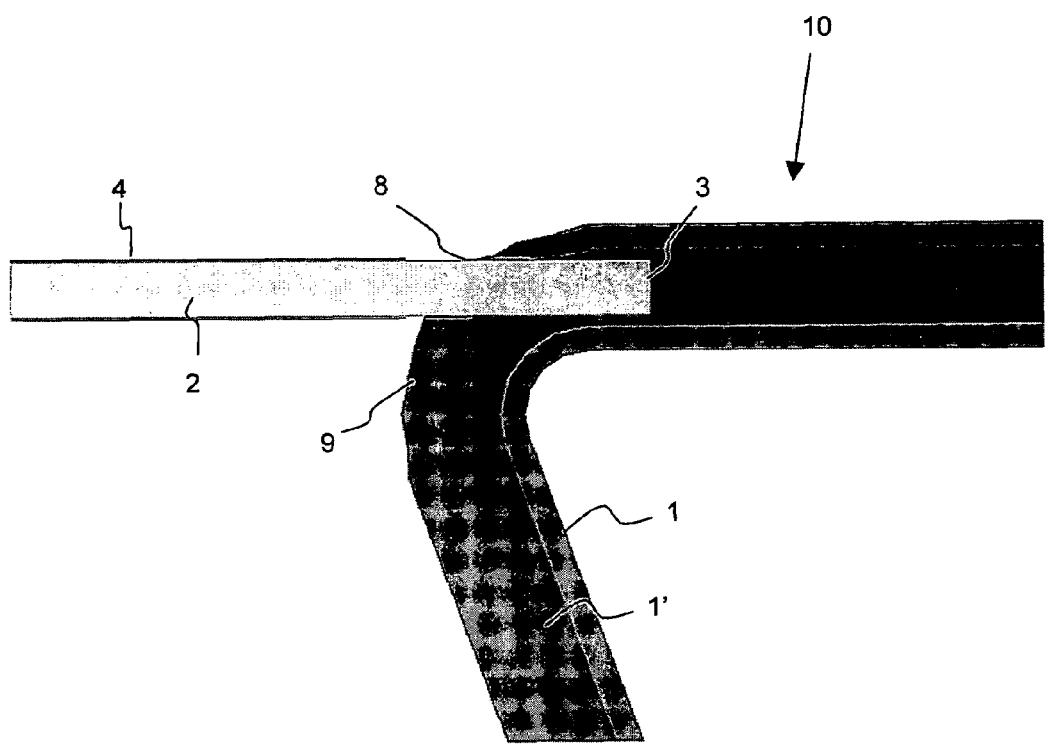
FIG. 2a shows a cross sectional side view of the fluidic device with a waveguide being inserted into the capillary via an opening, said capillary having one bending.

FIG. 2a refers to an embodiment of the fluidic device 10 being adapted to conduct a fluid along a fluid flow path 1' and to subject said fluid to light by use of a capillary 1. Said capillary 1 has one bending 9, which bending has an opening 8 at its outer curve in order to permit insertion of the waveguide 2 from outside into the capillary 1 or into the fluid flow path 1', respectively. The function of the waveguide 2 may be determined by connecting it either with a light emitting or with a light detecting device, which is not shown in FIG. 2a.

Figure 2C:
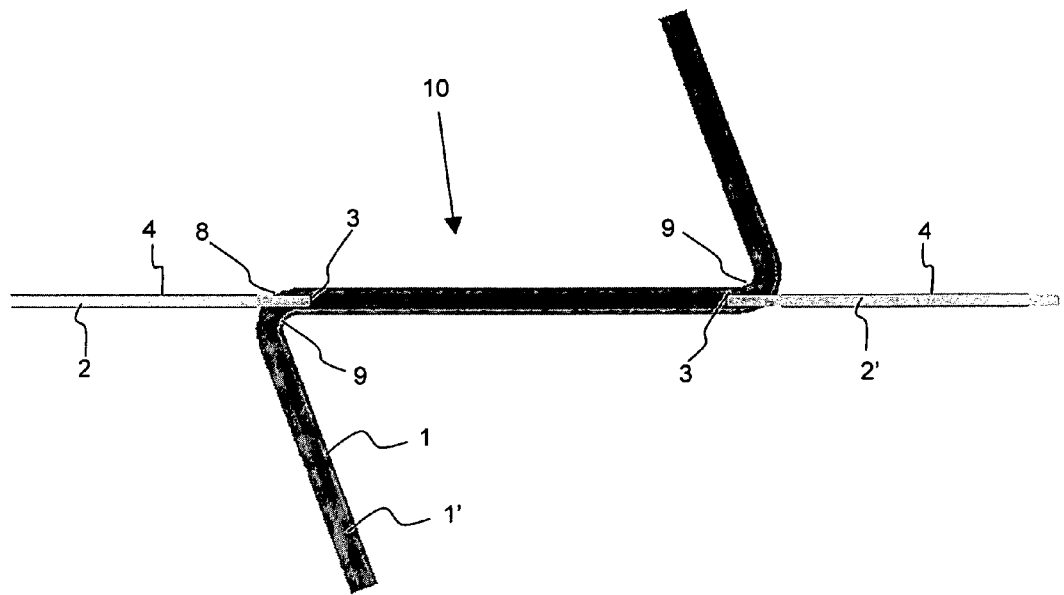
FIG. 2c shows a cross sectional side view of the fluidic device with a couple of waveguides being inserted via two openings into a capillary having two bendings.
Figure 2B:
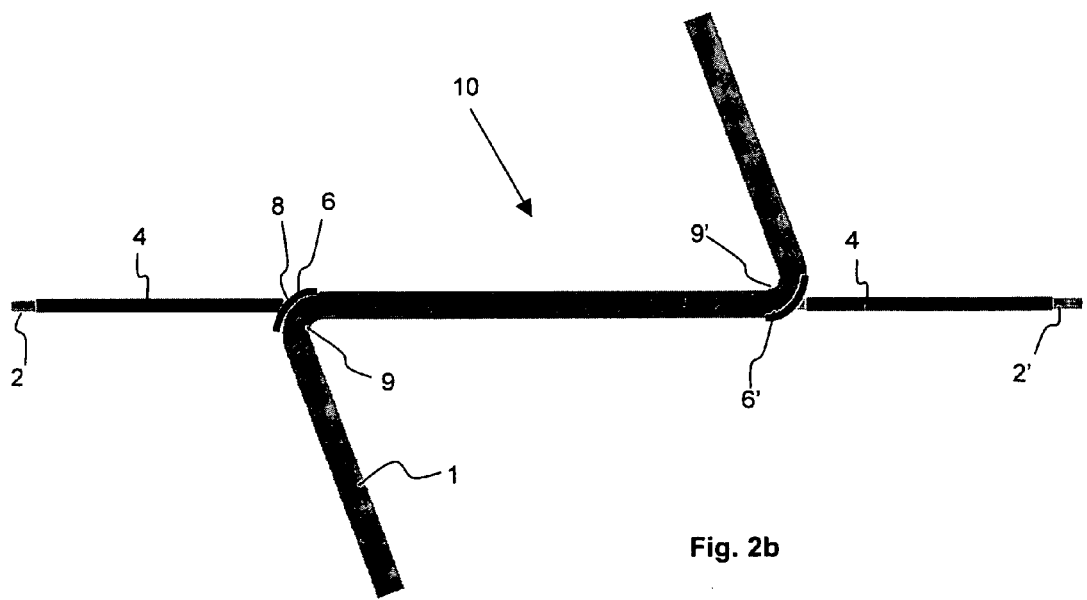
FIG. 2b shows a side view of the fluidic device with a couple of waveguides being inserted via two openings into a capillary having two bendings.

FIGS. 2b to 2c depict embodiments of the present invention comprising capillaries 1 which have two bendings 9,9' with the bending angles being approximately 60°. Other embodiments may have larger or smaller bending angles. As shown clearly by the cross sectional view of the device in FIG. 2c, the capillary 1 comprises two openings 8,8' at the outer curves of the bendings 9,9' in order to permit insertion of the waveguide 2 via the opening 8 and to permit insertion of the waveguide 2' via the opening 8' into the fluid flow path 1'. Thereby, the end faces 3,3' of the waveguides 2,2' are arranged to communicate optically inside the capillary, providing a light path 11 in between the end faces 3,3' and, hence, in between the two bendings 9,9'. The light path 11 between the facing waveguides 2,2' is accordingly shorter than the distanced between the bendings 9,9' is.

Furthermore, an extra sealing 6,6' is provided around the end faces 3,3' of the waveguides 2,2', see the side view of this embodiment which is displayed in FIG. 2b. The sealing material could be applied directly around the openings 8,8', whereby a fluid tight device 10 can be obtained. An additional effect based on the application of the sealing is the avoidance of light exiting at the fiber-to-capillary interface. Furthermore, the sealing 6,6' gives an extra stabilization of the coupling.

Generally, the sealing of the fiber-to-capillary interface, referring to the version when the capillary provides an opening for insertion of the waveguide, may be performed using advantageously molten quartz material that may result from welding the capillary. "Welding" herein means that the capillary is heated up to the melting point when the capillary is readily arranged, being inserted into the capillary via the opening. The quartz material of the capillary becomes highly viscous and moves slowly into the spaces of the annular gap around the waveguide in the opening.

Otherwise, one may apply an extra volume of molten quartz material, the quartz material being a filler material then, which is inserted in said annular gap or space which exists in between at the opening of the capillary and the waveguide at the coupling. Other sealing materials could be polymeric materials, such as polyetherketones, in particular polyetheretherketone, which is known generally by those skilled in the art to be a suitable sealing material for quartz devices. Of course, other suitable sealing materials might be used.

Figure 3A:
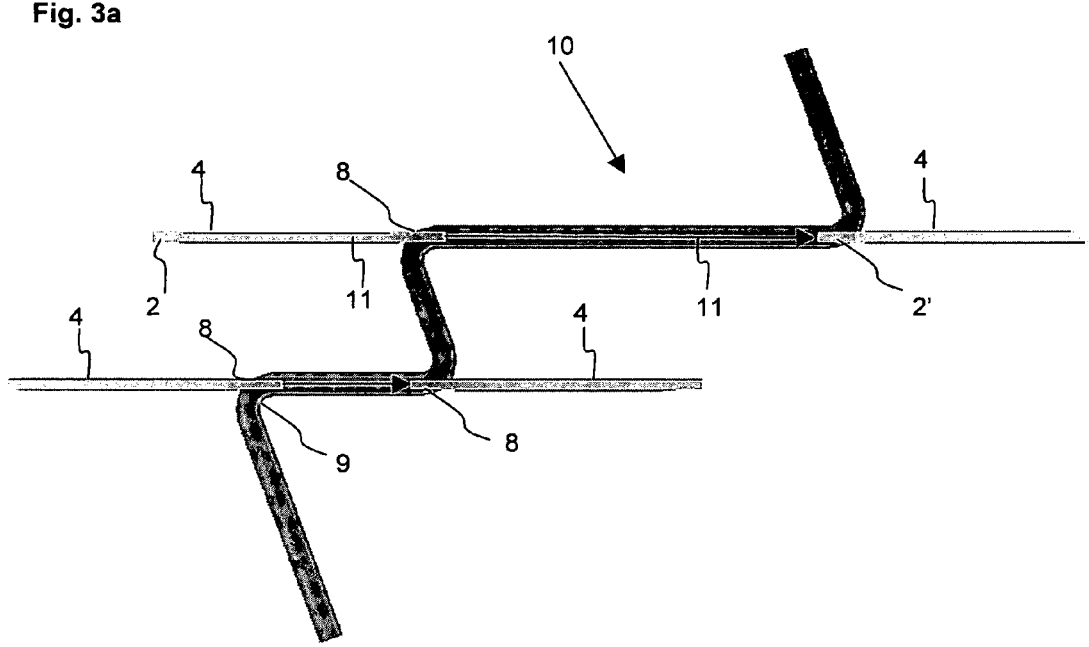
FIG. 3a shows a cross sectional side view of the fluidic device as "tandem version" with two couples of waveguides being inserted into the capillary having four bendings, each of which couple of waveguides entering and exiting the via two openings

FIG. 3a shows a cross sectional side view of the fluidic device as "tandem version" with two couples of waveguides 2,2' being inserted into the capillary 1 having four bendings 9, each of which couple of waveguides entering and exiting the capillary 1 via two openings 8,8'.

Figure 3B:
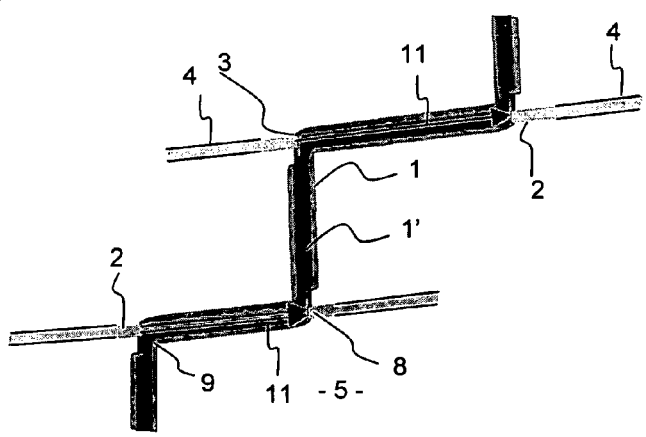
FIG. 3b shows a cross sectional side view of the fluidic device as "tandem version" with two couples of waveguides being docked via four docking spots to a capillary having four bendings.

FIG. 3b depicts a cross sectional side view of the fluidic device as "tandem version", too, but herein the coupling of the waveguides 2,2' to the capillary 1 is performed by docking, as depicted in FIGS. 1a to 1c. Herein, a number of four docking flat spots 7 with a capillary 1 having four bendings 9 is provided, permitting docking of two couples of waveguides 2,2'. It has to be taken into consideration that the principles of using the waveguides for detection of photochemical reactions may me realized; accordingly a couple of waveguides facing each other communicate optically due to their light emitting and light receiving properties, or both waveguides of a couple serve as light emitting devices.

Performing photochemistry in a "tandem version" may be most advantageously due to the increased light input, accordingly one may increase the conversion rate.

Referring to the use of the fluidic device 10 as detection device, FIG. 3a depicts the option of having different lengths of the light path 11 in one single device. This permits detection of different components: Since the fluid flow path 1' between a couple of two waveguides 2,2' serves as "detection cell", one might wish to have connected "detection cells" having different lengths and, hence, having different distances d, in order to focus on different component concentrations. Highly concentrated components could then be detected by use of the short light path 11 having a short distance d, whereas low concentrations could be detected by use of a long light path 11 having a long distance d.

The combination of both long and short light paths in one single device therefore allows the time saving detection of different concentrations in one step. Of course, one may increase the number of light paths by designing the fluid device 10 with an increased number of bendings, each bending facing another bending, allowing the coupling of a couple of waveguides according to one of the above depicted coupling methods: Insertion of the waveguide or coupling via a docking flat spot.

The embodiments of the present invention could be embedded in a stabilizing material, which stabilizing material might be advantageously quartz since the optical and chemical properties of a quartz embedding correspond ideally with the properties of the fluid device material. One could embed the fluidic device completely or only parts of it, providing at least stabilization for the fragile parts of the device, in particular for the waveguides or the waveguide-to-capillary interfaces. The embedding may prevent the capillary and waveguides from destruction and soiling One may wish to operate the fluidic device of the embodiments of the present invention batch wise, accordingly the fluid to be detected or to be subjected to a photochemical reaction could be filled in, then it would be kept inside the capillary and after the desired application is performed one might release the fluid, either into a waste disposal, or into another device for further use.

Other embodiments of the present invention refer to an integration of the fluid device, which is described above and is shown in the FIGS. 1a to 3b, in a fluidic flow through device:

Generally, the capillaries of the herein referred fluidic device should have at least one inlet for filling in the fluid; said inlet could serve as outlet, too, if the device is used in the batch mode. If otherwise the fluid device is used as a fluidic flow through device, at least one inlet and at least one outlet should be provided. Generally, the fluidic flow through device comprises a capillary to conduct the fluid, which capillary has one or more bendings. Furthermore, said bending is provided with a coupling option to provide a coupling of the capillary and a waveguide, which is adapted for emitting or receiving light. Whether the function of the waveguide is emitting or receiving light depends on the further components of the fluidic flow through device: Either the waveguide is connected to a light source, thereby being a light emitting device, or the waveguide is connected to a light detecting device, thereby it serves as a light receiving device. The light emitting source or the detector may be connected directly to the capillary or in a certain distance and the connection may include an interconnecting element.

If the fluidic flow through device has a plurality of bendings, not necessarily all of them need to be coupled to a waveguide. Furthermore, the fluidic flow through device comprises coupling of the inlet of the capillary with a conduit so that the fluid supply from a fluid source into the capillary can be realized using said conduit. It may additionally have a conduit being coupled to the outlet, so that the release of the fluid can be done via said second conduit. Of course one has to take into consideration that a plurality of inlets and/or outlets might let it seem to be useful to provide an supplying or releasing conduit for each inlet and outlet, respectively.

Coupling of the conduits to a master device would permit in-line detection of fluidic substance in an ongoing process, it offers several options to proceed with the released fluid such as recycling it into the process it after being detected or subjecting the fluid to further procedures without interrupting the process.

The capillary of the herein described fluidic flow through device should advantageously be made of the material which is suggested for the above capillary being part of the fluidic device; the waveguide should be made of quartz. Total reflectance of light inside the capillary and inside the waveguide is advantageously provided; accordingly coating of capillary and waveguides could be performed to achieve an increased guiding of light.

The coupling of the waveguide to the capillary could be realized either by docking the waveguide with its end face at a docking flat spot, provided at the outer curve of the bending, to the outer surface of the capillary, or the capillary comprises an opening at the outer curve of the bending in order to permit insertion of the waveguide via said opening into the capillary, so that it is located in the fluid flow path inside the capillary. Generally, the end faces of two waveguides being coupled to two facing bendings may communicate optically inside the capillary, thereby providing a light path in between the two bendings.

After all, one may generally optimize the optical measurements by equipping the capillaries of all embodiments of the herein disclosed invention with a texture in the region of the distance d. The capillary has an inner and an outer surface, which are both interfaces causing diffraction and reflection of the light guided from the light emitting waveguide to the light receiving waveguide. Providing a texture at the capillary inside or at its outside or both results in a multiple diffracting and refracting of the guided light inside the capillary, leading to an enhanced illumination of the capillary inside. This leads to an enhanced optical detection due to a reduction of the sensitivity of the device with respect to parameters influencing the measurement negatively. Such parameters might be changes of temperature of the detected fluid or vibrations of the fluid device in the master device.

One may coat the capillary, even a capillary which is textured at its outside, in the region of the distance d of the light path. The coating material could be advantageously a polyimide, an amorphous fluoropolymer, a coating dye or any other suitable coating material which provides total reflectance of the light inside the capillary.

Of course, the fluidic flow through device could be embedded in a stabilizing material in the same manner than the fluidic device can be embedded. Accordingly, the embedding material is quartz, as has been suggested before. One could embed the fluidic flow through device completely or only parts of it, depending on the need of stabilization and on the integration of said fluidic flow through device into a master device, e. g.

The above described embodiments of the fluidic device or the fluidic device as component in a fluidic flow through system could be manufactured by the following methods:

The capillary, which serves as fluid conductor which has at least one bending, is coupled to a waveguide. Said coupling is performed in that the end face of the waveguide is attached to the bending by heating the capillary at the place where a bending is desired until it can be deformed. The quartz material becomes highly viscous when heated, so that it can be bent when heated to the melting point. Bending is executed until the bending angle has the desired value. The above embodiments show bending angles of approximately 60° to 90°. The heating is maintained to keep the material deformable, and a flattening device is pressed onto the outer curve of the bending in a way that a portion of the bending outside is flattened and therefore provides a docking flat spot which is adapted for docking the waveguide to it.

One may wish perform the above method in another order: One may heat a capillary until it is highly viscous at the places where the bending is desired, but then one applies flattening device first, is pressing it onto the heated place until the desired docking flat spot is obtained. Maintaining the heating, one proceeds with the bending now. Bending is finished when the desired bending angle is achieved. Afterwards one may go ahead with the coupling of the waveguide:

The end face of the waveguide becomes fixed the docking flat spot by gluing or welding. The gluing or welding may include the application of extra volume of molten quartz material around the end face. Another possibility is applying of a polymeric material such as a polyetherketone like polyetheretherketone, or another suitable gluing material around the end face until the desired stability of the waveguide-to capillary interface is obtained.

A second method for coupling the waveguide to the capillary bending comprises the generating of an opening at the bending. This may be achieved in that the capillary is heated, at least partially, until it can be penetrated. The quartz material becomes highly viscous when heated to the melting point, so that it can be modeled or bent, respectively. Now, a penetrating device penetrates the capillary at the bending under maintenance of heating the capillary at the bending. When the desired opening is obtained the penetrating device is removed and the capillary may be cooled. If desired, one may provide the coupling of capillary and waveguide in that the waveguide is inserted into the opening when the capillary is still hot, so that the still viscous quartz material of the capillary may flow into the annular gap which exists between the opening and the inserted waveguide. The quartz material would close the gap then, providing a sealing. Now, one may let the capillary cool down.

If the capillary is cooled down directly after generating the opening, one may insert the waveguide later on. Then, the sealing of said gap can be achieved by adding an extra material: Molten quartz material or a polymeric material such as a polyetherketone like polyetheretherketone or a suitable gluing material, can be inserted in said gap, or it can be applied round the waveguide at the opening, providing a fluid-tight coupling of the waveguide and the capillary.

The penetrating of the heated capillary can be done by drilling a drilling tool through the capillary at the bending. The penetrating tool could be one of a diamond drilling tool, a drilling tool adapted to perform one of laser drilling and ultrasonic drilling, a punch, in particular a metal cone or a diamond cone.

What is claimed is:

1. A fluidic device adapted to subject a fluid to light and comprising:
    a capillary adapted for conducting the fluid and comprising at least one bending, and
    at least one waveguide having an end face adapted for at least one of emitting and receiving light, wherein the end face is coupled with said bending for at least one of emitting light into the fluid and receiving light from the capillary.

2. The fluidic device of claim 1, wherein a first and a second waveguide are comprised, and the end faces of which facing each other in a distanced, wherein an optical communication between the end faces is provided.

3. The fluidic device of claim 1, wherein the waveguide is a quartz fiber.

4. The fluidic device of claim 1, wherein the waveguide is coated at least partially, with the coating being one of a polyimide, a dye or any other suitable coating material which provides total reflectance of the light inside the waveguide.

5. The fluidic device of claim 1, wherein the end face is coupled to the capillary in that an opening is provided at the bending, adapted to permit insertion of the waveguide.

6. The fluidic device of claim 1, wherein the end face is coupled to the capillary in that a docking flat spot is provided at the bending adapted to permit docking of the waveguide with the capillary at the bending outside.

7. The fluidic device of claim 1, wherein the capillary is made of a material being one of an amorphous fluoropolymer or quartz, providing a total reflectance of the light inside said capillary.

8. The fluidic device of claim 2, wherein the capillary has an inner and an outer surface and wherein at least one of the inner and an outer surface has a texture in the region of the distanced, said texture being adapted to provide multiple diffracting and refracting of the guided light inside the capillary.

9. The fluidic device of claim 2, wherein the capillary is coated, at least in the region of the distanced, with the coating being one of a polyimide, amorphous fluoropolymer, a dye or any other suitable coating material which provides total reflectance of the light inside the capillary.

10. The fluidic device of claim 1, wherein a sealing is provided at the coupling,
said sealing comprising at least one selected from the group consisting of:
molten quartz material, with the quartz material resulting from welding the capillary,
molten quartz material, with the quartz material being a filler material, which is inserted in a gap provided at the opening, and
a polymeric material,
the sealing being adapted to provide a fluid-tight coupling of the waveguide and the capillary.

11. The fluidic device of claim 6, wherein the docking is provided at the docking flat spot by adding at least one material selected from the group consisting of:
an extra volume of molten quartz material around the end face
a polymeric material,
a polyetherketone,
polyetheretherketone, and
a suitable gluing material,
around the end face.

12. The fluidic device of claim 1, wherein the fluidic device is at least partially embedded in a stabilizing material, in particular into quartz, adapted to provide at least one of stabilization and preventing the capillary from destruction and soiling.

13. A fluidic flow through device adapted for subjecting a fluid to light and comprising:
a capillary adapted for conducting said fluid and comprising at least one bending, said capillary having an inlet and an outlet,
at least one waveguide having an end face adapted for at least one of emitting and receiving light, wherein a coupling couples the end face with said bending for at least one of emitting light into the fluid and receiving light from the capillary, and
a conduit adapted for at least one of supplying said capillary with fluid or releasing the fluid, and being coupled to at least one of the inlet or the outlet.

14. The fluidic flow through device of claim 13, comprising:
a first and a second waveguide, the end faces of which facing each other in a distanced, wherein an optical communication between the end faces is provided.

15. The fluidic flow through device of claim 13, wherein the capillary has an inner and an outer surface and wherein at least one of the inner and an outer surface has a texture in the region of the distance d, said texture being adapted to provide multiple diffracting and refracting of the guided light inside the capillary.

16. The fluidic flow through device of claim 13, wherein at least one of the waveguide and the capillary is coated at least partially, with the coating being at least one selected from the group consisting of: a polyimide, an amorphous fluoropolymer, a dye and any other suitable coating material which provides total reflectance.

17. The fluidic flow through device of claim 13, wherein the coupling of the end face of the waveguide to the capillary is provided by one of the following features:
an opening being provided at the bending, adapted to permit insertion of the waveguide, or
a docking flat spot being provided at the bending, adapted to permit docking of the waveguide with the capillary at the bending outside.

18. The fluidic flow through device of claim 13, wherein a sealing is provided at the opening, said sealing comprising at least one material selected from the group consisting of:
molten quartz material, with the quartz material resulting from welding the capillary,
molten quartz material, with the quartz material being a filler material, which is inserted in a gap provided at the opening,
a polymeric material,
a polyetherketone, and
polyetheretherketone,
the sealing being adapted to provide a fluid-tight coupling of the waveguide and the capillary.

19. The fluidic flow through device of claim 13, wherein the docking is provided at the docking flat spot by adding at least one selected from the group comprising:
an extra volume of molten quartz material around the end face
a polymeric material,
a polyetherketone,
polyetheretherketone, and
a suitable gluing material around the end face.

20. The fluidic flow through device of claim 13, wherein the fluidic device is at least partially embedded in a stabilizing material, adapted to provide at least one of stabilization and preventing the capillary from destruction and soiling.

21. A method comprising:
providing a fluidic device adapted to subject a fluid to light and having a capillary adapted for conducting the fluid and including at least one bending, and having at least one waveguide with an end face adapted for at least one of emitting and receiving light, and
coupling the end face with said bending for at least one of emitting light into the capillary and receiving light from the capillary.

22. The method of claim 21, wherein coupling comprises at least one feature selected from the group consisting of:
heating the capillary at the bending until the capillary is deformable,
bending the capillary until a bending is generated,
maintaining the heating, and
flattening a portion of the bending outside by applying a flattening device, whereby a docking flat spot is provided adapted for docking the waveguide.

23. The method of claim 21, comprising at least one feature selected from the group consisting of:
docking the waveguide with the docking flat spot, and
fixing the waveguide at the docking flat spot by gluing or welding.

24. The method of claim 21, wherein coupling comprises:
generating an opening at the bending in that a penetrating device penetrates the capillary at the bending.

25. The method of claim 21, comprising at least one feature selected from the group consisting of:
heating the capillary, at least partially, until the capillary is deformable,
modeling the capillary until a bending is generated,
maintaining the heating, and
performing the penetrating.

26. The method of claim 21, comprising at least one feature selected from the group consisting of:
heating the capillary, at least partially, until the capillary is deformable,
modeling the capillary until a bending is generated,
cooling the capillary, and
performing the penetrating by drilling a drilling tool through the capillary at the bending.

27. The method of claim 24, wherein penetrating comprises applying at least one tools selected from the group consisting of:
diamond drilling tool,
drilling tool adapted to perform one of laser drilling and ultrasonic drilling, and
a punch, in particular a metal cone or a diamond cone.

* * * * *

UNITED STATES PATENT AND TRADEMARK OFFICE
CERTIFICATE OF CORRECTION

PATENT NO. : 7,403,280 B2  Page 1 of 1
APPLICATION NO. : 11/266679
DATED : July 22, 2008
INVENTOR(S) : Beigel et al.

It is certified that error appears in the above-identified patent and that said Letters Patent is hereby corrected as shown below:

In column 8, line 55, in Claim 2, delete "distanced," and insert -- distance d, --, therefor.

In column 9, line 10, in Claim 8, delete "distanced," and insert -- distance d, --, therefor.

In column 9, line 14, in Claim 9, delete "distanced," and insert -- distance d, --, therefor.

In column 9, line 63, in Claim 14, delete "distanced," and insert -- distance d, --, therefor.

Signed and Sealed this

Seventh Day of October, 2008

JON W. DUDAS
*Director of the United States Patent and Trademark Office*